(12) United States Patent
Kim et al.

(10) Patent No.: US 8,036,501 B2
(45) Date of Patent: Oct. 11, 2011

(54) PRINTED CIRCUIT BOARD FOR OPTICAL WAVEGUIDES AND METHOD OF MANUFACTURING THE SAME

(75) Inventors: Sang Hoon Kim, Gunpo-si (KR); Han Seo Cho, Daejeon-si (KR); Jae Hyun Jung, Ansan-si (KR); Joon Sung Kim, Suwon-si (KR)

(73) Assignee: Samsung Electro-Mechanics Co., Ltd., Suwon (KR)

( * ) Notice: Subject to any disclaimer, the term of this patent is extended or adjusted under 35 U.S.C. 154(b) by 0 days.

(21) Appl. No.: 12/588,453

(22) Filed: Oct. 15, 2009

(65) Prior Publication Data

US 2011/0019959 A1 Jan. 27, 2011

(30) Foreign Application Priority Data

Jul. 23, 2009 (KR) .................. 10-2009-0067510

(51) Int. Cl.
*G02B 6/12* (2006.01)

(52) U.S. Cl. ........................................ 385/14

(58) Field of Classification Search .................. None
See application file for complete search history.

(56) References Cited

U.S. PATENT DOCUMENTS

2010/0316330 A1 * 12/2010 Kim et al. ............... 385/14

FOREIGN PATENT DOCUMENTS

| JP | 2001-311846 | 11/2001 |
| KR | 10-2009-0047109 | 5/2009 |

* cited by examiner

*Primary Examiner* — Jerry Rahll

(57) ABSTRACT

The present invention relates to a printed circuit board for optical waveguides and a method of manufacturing the same. The present invention provides a printed circuit board for optical waveguides includes: a base substrate; an optical waveguide that is formed on an upper middle of the base substrate and includes a lower clad, a core formed on an upper middle of the lower clad, and an upper clad formed on the lower clad to surround an upper surface and a side surface of the core; and a side substrate that is formed on the base substrate and has a through hole, through which the optical waveguide penetrates, provided at the middle thereof and a circuit pattern formed therein and a method of manufacturing a printed circuit board for optical waveguides.

7 Claims, 9 Drawing Sheets

PRINTED CIRCUIT BOARD FOR OPTICAL WAVEGUIDES AND METHOD OF MANUFACTURING THE SAME

CROSS REFERENCES RELATED APPLICATIONS

The present application claims priority under 35 U.S.C. 119 and 35 U.S.C. 365 to Korean Patent Application No. 10-2009-0067510 filed on Jul. 23, 2009, which is hereby incorporated by reference in its entirety.

BACKGROUND OF THE INVENTION

1. Field of the Invention

The present invention relates to a printed circuit board for optical waveguides and a method of manufacturing the same, and more specifically, to a printed circuit board for optical waveguides wherein a center in a thickness direction of the printed circuit board for optical waveguides is formed with a circuit pattern and a method of manufacturing the same.

2. Description of the Related Art

Generally, a printed circuit board (PCB) means a circuit board wherein various kinds of many parts are densely mounted on a panel of phenol resin or epoxy resin and circuits connecting between each part are compressed and fixed on a surface of the panel made of resin.

Such a printed circuit board is manufactured by attaching a thin plate, such as copper, etc., to one surface of an insulating plate of phenol resin or an insulating plate of epoxy resin, etc., and then etching it depending on a wiring pattern of a circuit in order to form necessary circuits and boring holes in order to attach and mount parts thereon. Meanwhile, the printed circuit board is classified into a single side board, a double side board, a multilayer board, etc. Generally, as the number of layers is increased, the mounting strength of parts becomes excellent, such that the multilayer board is used for high-precision products.

In the case of manufacturing the printed circuit board according to the related art, an inner layer and an outer layer of the printed circuit board are formed by forming the circuit patterns on a copper plate; however, a printed circuit board including optical waveguides, which can transmit and receive signals using light, has been currently manufactured.

However, the printed circuit board including the existing optical waveguides has low bending reliability since the circuit pattern is eccentrically positioned outside in a thickness direction of the printed circuit board.

SUMMARY OF THE INVENTION

Therefore, the present invention proposes to solve the above-mentioned problems. It is an object of the present invention to provide a printed circuit board for optical waveguides capable of improving the bending reliability of the printed circuit board for optical waveguides by forming a circuit pattern on a center in a thickness direction of the printed circuit board for optical waveguides and implementing a circuit layer of at least three layers on one printed circuit board for optical waveguides and a method of manufacturing the same.

In order to accomplish the above-mentioned object, there is provided a printed circuit board for optical waveguides, including: a base substrate; an optical waveguide that is formed on an upper middle of the base substrate and includes a lower clad, a core formed on an upper middle of the lower clad, and an upper clad formed on the lower clad to surround an upper surface and a side surface of the core; and a side substrate that is formed on the base substrate and has a through hole, through which the optical waveguide penetrates, provided at the middle thereof and a circuit pattern formed therein.

Herein, the first circuit pattern may have thickness thinner than that of the optical waveguide.

Further, the first circuit pattern may have thickness thinner than that of the core.

In addition, the upper surface of the first circuit pattern may be formed to be lower than the upper surface of the optical waveguide and the lower surface thereof may be formed to be higher than the lower surface of the optical waveguide.

Moreover, the upper surface of the first circuit pattern may be formed to be lower than the upper surface of the core and the lower surface thereof may be formed to be higher than the lower surface of the core.

Also, the printed circuit board for optical waveguides may further include a second circuit pattern that is formed inside the side substrate and has a lower surface contacting the upper surface of the base substrate.

Further, the printed circuit board for optical waveguides may further include a second circuit pattern that is formed inside the base substrate and has an upper surface contacting the lower surface of the side substrate.

In addition, the printed circuit board for optical waveguides may further include an upper substrate that is formed on the side substrate including the optical waveguide.

Moreover, the upper substrate may include a third adhesive layer and a third insulating layer that are sequentially stacked.

Further, the printed circuit board for optical waveguides may further include a third circuit pattern that is formed inside the third adhesive layer and has an upper surface contacting the third insulating layer.

In addition, the printed circuit board for optical waveguides may further include a third circuit pattern that is formed inside the third insulating layer and has a lower surface contacting the third adhesive layer.

Also, the printed circuit board for optical waveguides may further include an outer layer substrate that is stacked on the lower surface of the base substrate and the upper surface of the side substrate including the optical waveguide; a fourth circuit pattern that is formed on the upper surface of the outer substrate; and a solder resist that is formed on the outer layer substrate to cover the fourth circuit pattern.

In addition, the printed circuit board for optical waveguides may further include an upper substrate that is formed between the upper surface of the side substrate including the optical waveguide and the outer layer substrate.

In order to accomplish the above-mentioned object, there is provided a method of manufacturing a printed circuit board for optical waveguides according to one embodiment of the present invention, including: preparing a base substrate; forming an optical waveguide, which includes a lower clad, a core formed on an upper middle of the lower clad, and an upper clad formed on the lower clad to surround an upper surface and a side surface of the core, on an upper middle of the base substrate; disposing a side substrate including a first side substrate that has a through hole, through which the optical waveguide penetrates, provided at the middle thereof and a first circuit pattern formed therein and a second side substrate disposed on the first side substrate on the upper part of the base substrate on which the optical waveguide is formed; disposing an upper substrate on the side substrate on which the through hole is formed; and stacking the side substrate and the upper substrate on the base substrate on which the optical waveguide is formed.

Herein, the first circuit pattern may have thickness thinner than that of the optical waveguide.

Further, the first circuit pattern may have thickness thinner than that of the core.

In addition, in the stacking the side substrate and the upper substrate on the base substrate on which the optical waveguide is formed, the upper surface of the first circuit pattern may be positioned to be lower than the upper surface of the optical waveguide and the lower surface thereof may be positioned to be higher than the lower surface of the optical waveguide.

Moreover, in the stacking the lateral substrate and the upper substrate on the base substrate on which the optical waveguide is formed, the upper surface of the first circuit pattern may be positioned to be lower than the upper surface of the core and the lower surface thereof may be positioned to be higher than the lower surface of the core.

Also, in the preparing the base substrate, any one of an insulating layer, a metal foil, and a laminate material thereof may be prepared as the base substrate.

In addition, when preparing the laminate material of the insulating layer and the metal foil are prepared as the base substrate, the method of manufacturing the printed circuit board for optical waveguides may further include forming a second circuit pattern on the insulating layer by patterning the metal foil.

Moreover, in the disposing the upper substrate, the upper substrate may include the adhesive layer and the insulating layer disposed on the adhesive layer.

Also, the lower surface of the insulating layer may be formed with a third circuit pattern.

In order to accomplish the above-mentioned object, there is provided a method of manufacturing a printed circuit board for optical waveguides according to another embodiment of the present invention, including: preparing a base substrate; stacking a side substrate including a first side substrate that has a through hole provided at the middle thereof and a first circuit pattern formed on an upper surface thereof and a second side substrate disposed on the first side substrate on the base substrate; and forming an optical waveguide, which includes a lower clad, a core formed on an upper middle of the lower clad, and an upper clad formed on the lower clad to surround an upper surface and a side surface of the core, inside the through hole of the side substrate.

Herein, the stacking the side substrate may include: disposing a first side substrate that has a through hole provided at the middle thereof and a first circuit pattern formed on the upper surface thereof and a second side substrate on the base substrate; and stacking the first side substrate and the second side substrate on the base substrate.

In addition, the stacking the side substrate may include: disposing a first side substrate, which has a through hole provided at the middle thereof, on the base substrate; disposing a metal foil on the first side substrate; stacking the first side substrate and the metal foil on the base substrate; forming a first circuit pattern on the first side substrate by removing a part of the metal part; and stacking a second side substrate, which has a through hole provided at the middle thereof, on the first side substrate on which the first circuit pattern is formed, similar to the first side substrate.

In addition, the optical waveguide may have thickness thicker than that of the first circuit pattern.

Further, the core may have thickness thicker than that of the first circuit pattern.

Moreover, in the forming the optical waveguide, the upper surface of the first circuit pattern may be positioned to be lower than the upper surface of the optical waveguide and the lower surface of the first circuit pattern may be positioned to be higher than the lower surface of the optical waveguide.

Also, in the forming the optical waveguide, the upper surface of the first circuit pattern may be positioned to be lower than the upper surface of the core and the lower surface of the first circuit pattern may be positioned to be higher than the lower surface of the core.

In addition, the method of manufacturing a printed circuit board for optical waveguides may further include after the forming the optical waveguide, stacking the upper substrate on the side substrate including the optical waveguide.

In order to accomplish the above-mentioned object, there is provided a method of manufacturing a printed circuit board for optical waveguides according to still another embodiment of the present invention, including: preparing a first metal foil; forming an optical waveguide, which includes a lower clad, a core formed on an upper middle of the lower clad, and an upper clad formed on the lower clad to surround an upper surface and a side surface of the core, on an upper middle of the first metal foil; disposing a side substrate including a first side substrate that has a through hole, through which the optical waveguide penetrates, provided at the middle thereof and a first circuit pattern formed on the upper surface thereof and a second side substrate stacked on the first side substrate on the first metal foil on which the optical waveguide is formed; sequentially stacking an adhesive layer and a second metal foil on the side substrate including the optical waveguide; and forming a second circuit pattern on the lower surface of the first side substrate and forming a third circuit pattern on the upper surface of the adhesive layer by removing a part of the first metal foil and the second metal foil.

Herein, the method of manufacturing a printed circuit board for optical waveguides may further include after forming a second circuit pattern on the lower surface of the first side substrate and forming a third circuit pattern on the upper surface of the adhesive layer by removing a part of the first metal foil and the second metal foil, forming a base substrate covering the second circuit pattern on the lower surface of the first side substrate and forming an insulating layer covering the third circuit pattern on the upper surface of the adhesive layer.

Further, the first circuit pattern may have thickness thinner than that of the core.

Also, in the stacking the side substrate, the upper surface of the first circuit pattern may be positioned to be lower than the upper surface of the core and the lower surface thereof may be positioned to be higher than the lower surface of the core.

As described above, with the printed circuit board for optical waveguides and the method of manufacturing the same according to the present invention, the circuit patterns formed on the side substrate are positioned at the central part in the thickness direction of the printed circuit board for optical waveguides as compared to the core of the optical waveguide, thereby making it possible to minimize the effect of stress on the circuit patterns when the printed circuit board of optical waveguides is bent.

Therefore, the present invention can prevent the circuit pattern from being broken when the printed circuit board for optical waveguides is bent, thereby making it possible to improve the bending reliability of the printed circuit board for optical waveguides.

In addition, the present invention has an advantage capable of implementing the circuit layer of at least three layers on one printed circuit board for optical waveguide.

DETAILED DESCRIPTION OF THE PREFERRED EMBODIMENTS

Hereinafter, exemplary embodiments of a printed circuit board for optical waveguides and a method of manufacturing the same according to the present invention will be described with reference to the accompanying drawings. The exemplary embodiments of the present invention to be described below are provided so that those skilled in the art to which the present invention pertains can fully carry out the present invention. Therefore, the present invention may be modified in many different forms and it should not be limited to the embodiments set forth herein. In the drawings, the thickness and the size of the device may be exaggerated for the convenience. Like reference numerals designate like components throughout the specification.

<Embodiment of a Structure of a Printed Circuit Board for Optical Waveguides>

A printed circuit board for optical waveguides according to exemplary embodiments of the present invention will be described in detail with reference to FIGS. 1 to 5.

Figure 1:
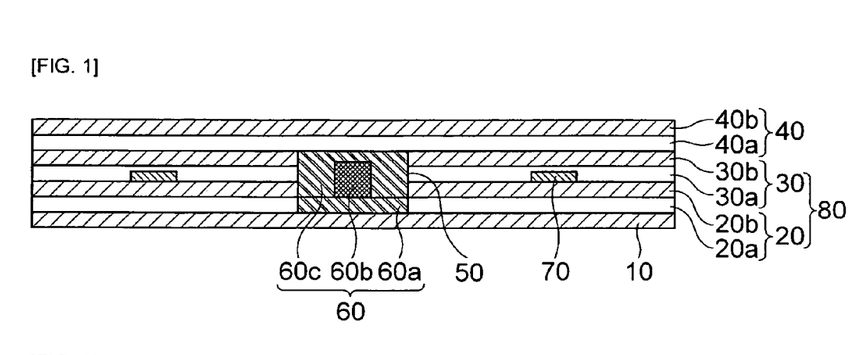
FIG. 1 is a cross-sectional view showing a printed circuit board for optical waveguides according to a first embodiment of the present invention.
Figure 2:
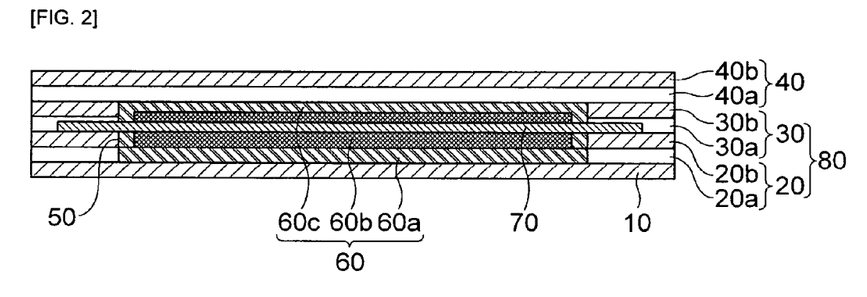
FIG. 2 is a side view showing the printed circuit board for optical waveguides according to the first embodiment of the present invention.
Figure 3:
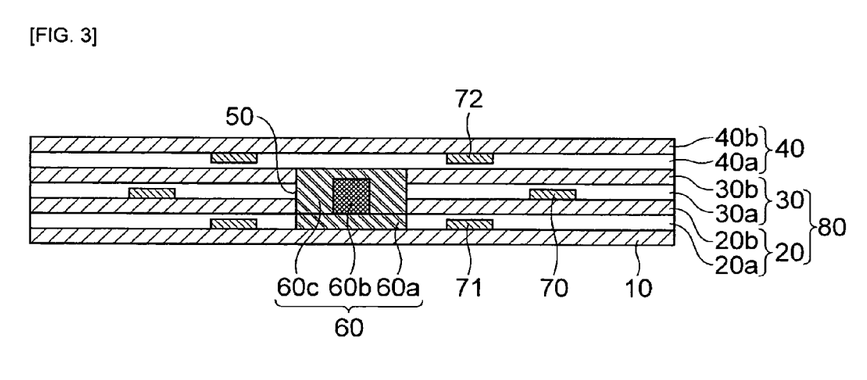
FIG. 3 is a cross-sectional view showing a printed circuit board for optical waveguides according to a second embodiment of the present invention.
Figure 4:
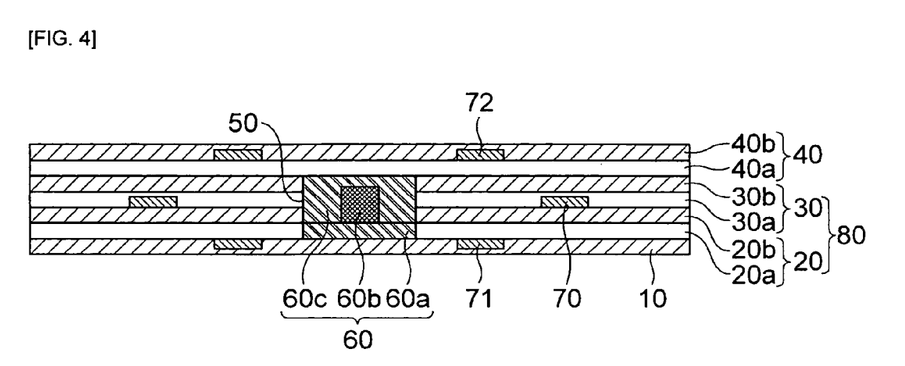
FIG. 4 is a side view showing a printed circuit board for optical waveguides according to a third embodiment of the present invention.
Figure 5:
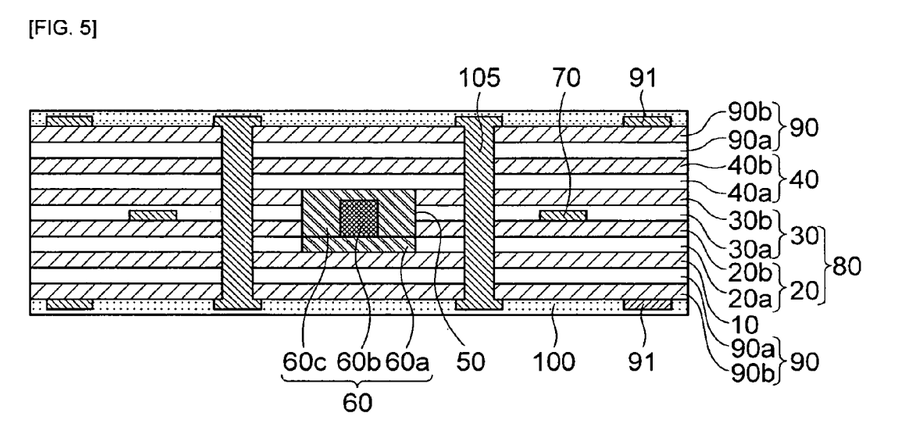
FIG. 5 is a side view showing a printed circuit board for optical waveguides according to a fourth embodiment of the present invention.

FIG. 1 is a cross-sectional view showing a printed circuit board for optical waveguides according to a first embodiment of the present invention and FIG. 2 is a side view showing the printed circuit board for optical waveguides according to the first embodiment of the present invention. FIG. 3 is a cross-sectional view showing a printed circuit board for optical waveguides according to a second embodiment of the present invention, FIG. 4 is a cross-sectional view showing a printed circuit board for optical waveguides according to a third embodiment of the present invention, and FIG. 5 is a cross-sectional view showing a printed circuit board for optical waveguides according to a fourth embodiment of the present invention.

First, the printed circuit board for optical waveguides according to the first embodiment of the present invention includes a base substrate 10, an optical waveguide 60 that is formed on an upper middle of the base substrate 10, and a side substrate 80 that is formed on the base substrate 10, has a through hole 50, through which the optical waveguide 60 penetrates, at a middle thereof, and has a first circuit pattern 70 formed inside the side substrate 80, as shown in FIGS. 1 and 2.

An upper substrate 40 is formed on the side substrate 80 including the optical waveguide 60. Herein, the upper substrate 40 may not be formed.

The base substrate 10 may be made of an insulating layer such as polyimide, etc. In addition, the base substrate 10 may be made of a metal foil, such as a copper foil (Cu foil), etc., instead of the insulation layer or may be made of a laminate material of the insulating layer and the metal foil, etc.

The optical waveguide 60 formed on the base substrate 10 includes a lower clad 60a, a core 60b that is formed on an upper middle of the lower clad 60a, and an upper clad 60c that is formed on the lower clad 60a to surround an upper surface and a side surface of the core 60b.

Herein, the lower clad 60a and the upper clad 60c may be made of a material prepared by adding additives for controlling a refractive index, etc., to polyimide, epoxy based materials, or acryl based materials, etc.

The lower clad 60a and the core 60b surrounded by the upper clad 60c may be made of a material prepared by adding additives for controlling a refractive index, etc., to polyimide, epoxy based materials, or acryl based materials, etc., similar to the lower clad 60a and the upper clad 60c.

At this time, the core 60b, which performs a function as a channel moving optical signals, may be made of a material having a refractive index higher than that of the lower clad 60a and the upper clad 60c surrounding the core 60b in order to efficiently transmit the optical signals.

The side substrate 80 may include the through hole 50, through which the optical waveguide 60 penetrates, provided at the middle thereof and a first side substrate 20 and a second side substrate 30 that are sequentially stacked.

The first side substrate 20 configuring the side substrate 80 may include a first adhesive layer 20a and a first insulating layer 20b that are sequentially stacked and the second side substrate 30 may include a second adhesive layer 30a and a second insulating layer 30b that are sequentially stacked.

Herein, the first and second adhesive layers 20a and 30a may be made of an epoxy adhesive and the first and second insulating layers 20b and 30b may be made of polyimide, etc.

The present embodiment shows and describes the side substrate 80 including the first and second side substrates 20 and 30 that are stacked, which shows only two side substrates for convenience of explanation. Therefore, the present embodiment is not limited thereto.

The inside of the side substrate 80 is formed with the first circuit pattern 70 as described above. The first circuit pattern 70 may be formed inside the second adhesive layer 30a so that the lower surface of the first circuit pattern 70 contacts the upper surface of the first insulating layer 20b.

In particular, in the printed circuit board for optical waveguides according to the first embodiment of the present invention, the first circuit pattern 70 may be formed to have thickness thinner than that of the optical waveguide 60. At this time, the first circuit pattern 70 is preferably formed so that the upper surface of the first circuit pattern 70 is lower than that of the optical waveguide 60 and the lower surface thereof is higher than the lower surface of the optical waveguide 60.

More preferably, the first circuit pattern 70 may be formed to have thickness thinner than that of the core 60b configuring the optical waveguide 60. At this time, the first circuit pattern 70 may be formed so that the upper surface of the first circuit pattern 70 is lower than that of the core 60 and the lower surface thereof is higher than the lower surface of the core 60b.

In other words, the printed circuit board for optical waveguides according to the embodiment of the present invention is formed at the center in a thickness direction of the board as compared to the core 60b of the optical waveguide 60.

Figure 8A:
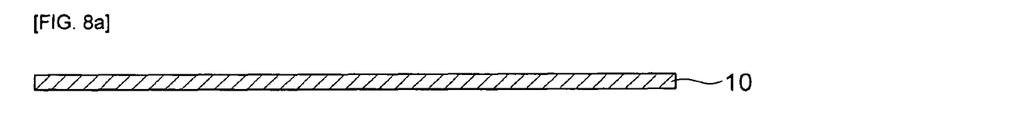
FIGS. 8A to 8I are process cross-sectional views sequentially shown for explaining still another method of manufacturing the printed circuit board for optical waveguides according to the first embodiment of the present invention.
Figure 8B:
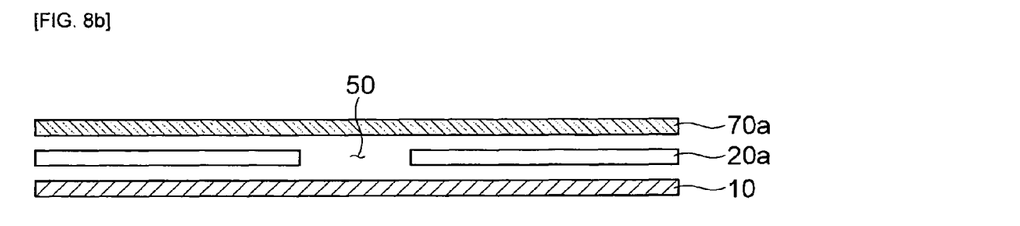
Figure 8C:
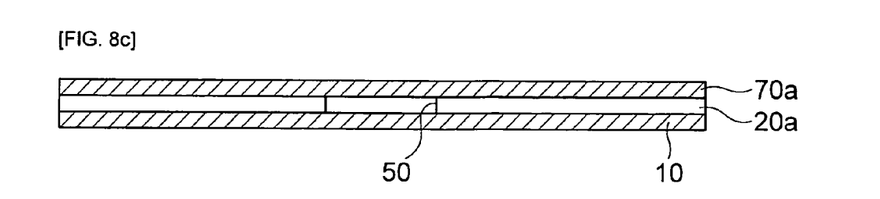
Figure 8D:
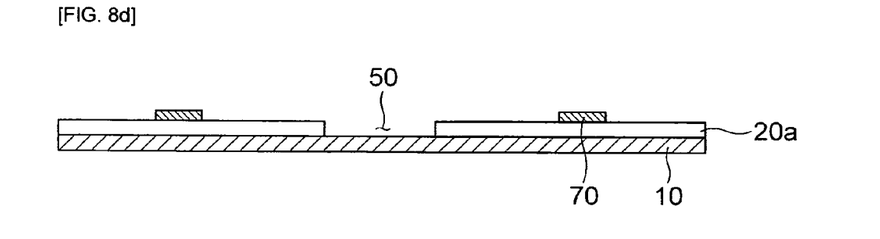
Figure 8E:
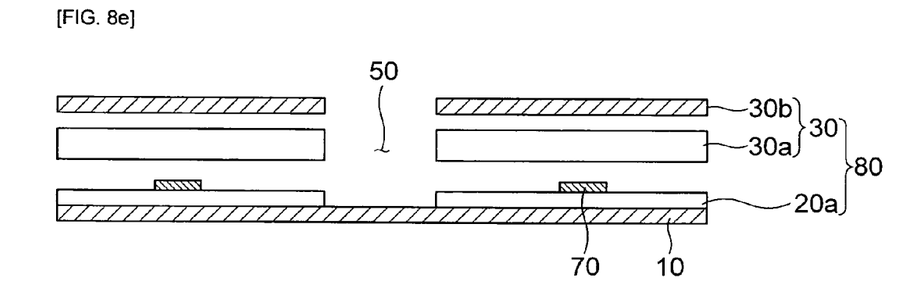
Figure 8F:
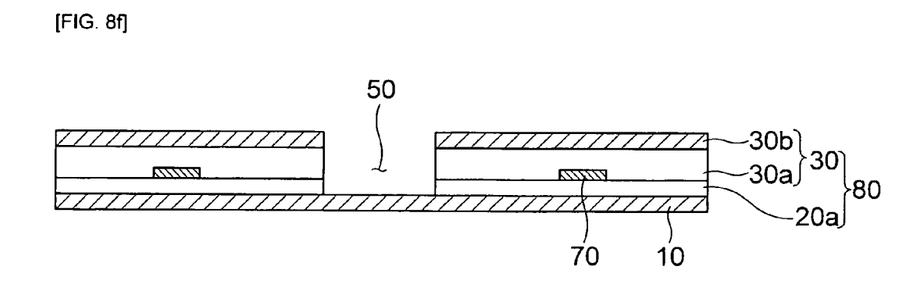
Figure 8G:
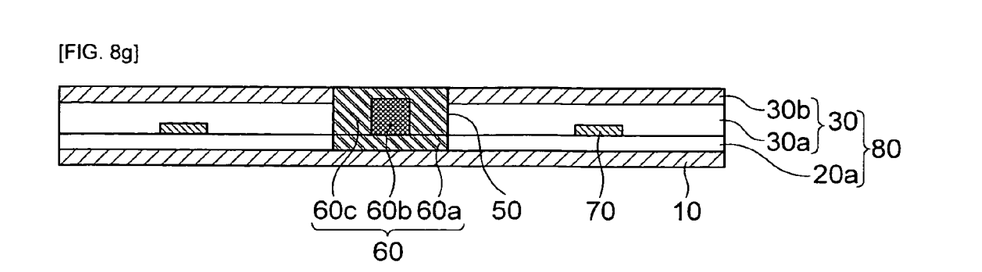
Figure 8H:
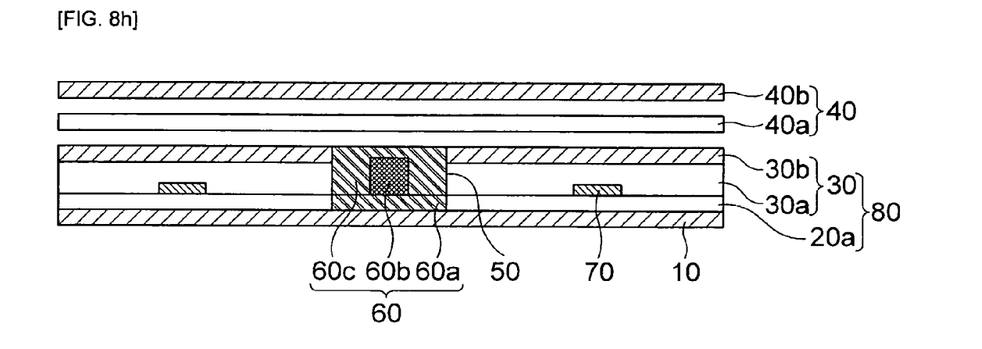
Figure 8I:
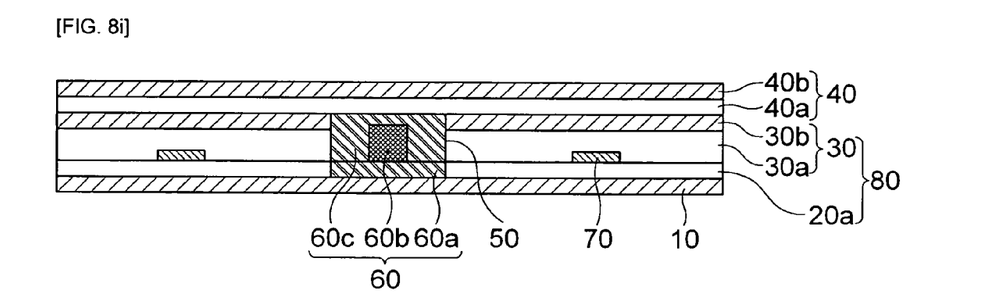

Meanwhile, the first side substrate 20 may be include the first adhesive layer 20a and the first insulating layer 20b that are sequentially stacked as shown in FIG. 1, but may be include the first adhesive layer 20a as shown in FIG. 8I.

In this case, the first circuit pattern 70 may be formed inside the second adhesive layer 30a so that the lower surface of the first circuit pattern 70 contacts the first adhesive layer 20a.

The upper substrate 40, which is formed on the side substrate 80 including the optical waveguide 60, may include a third adhesive layer 40a and a third insulating layer 40b that are sequentially stacked.

The third adhesive layer 40a may be made of an epoxy adhesive, etc., and the third insulating layer 40b may be made of polyimide, etc.

With the printed circuit board for optical waveguides according to the first embodiment of the present invention as described above, the first circuit pattern 70 is formed on the central part in a thickness direction of the printed circuit board for optical waveguide, that is, on a bending neural axis, such that when the printed circuit board for optical waveguides is bent, the effect of stress on the first circuit pattern 70 is minimized, thereby making it possible to prevent the first circuit pattern 70 from being broken.

Therefore, the first embodiment of the present invention can provide the printed circuit substrate for optical waveguide having the excellent bending reliability.

Next, a printed circuit board for optical waveguides according to the second embodiment of the present invention will be described in detail with reference to FIG. 3.

As shown in FIG. 3, a configuration of the printed circuit board for optical waveguide according to the second embodiment of the present invention is approximately similar to the configuration of the printed circuit board of optical waveguides according to the first embodiment of the present invention. However, the second embodiment is different from the first embodiment only in that it further includes a second circuit pattern 71 formed inside the side substrate 80 and having a lower surface contacting the upper surface of the base substrate 10.

Herein, the second circuit pattern 71 may be formed inside the first adhesive layer 20a configuring the side substrate 80.

Further, the printed circuit board for optical waveguides according to the second embodiment of the present invention may further include a third circuit pattern 72 that is formed inside the third adhesive layer 40a configuring the upper substrate 40 and has an upper surface contacting the third insulating layer 40b stacked on the third adhesive layer 40a.

The printed circuit board for optical waveguides according to the second embodiment of the present invention as described above can obtain the same action and effect as the first embodiment of the present invention and has an advantage capable of implementing a circuit layer of at least three layers on one printed circuit board for optical waveguides by forming the first, second, and third circuit patterns 70, 71, and 72 inside the printed circuit board for optical waveguides.

Next, the printed circuit board for optical waveguides according to the third embodiment of the present invention will be described in detail with reference to FIG. 4.

As shown in FIG. 4, a configuration of the printed circuit board for optical waveguide according to the third embodiment of the present invention is approximately similar to the configuration of the printed circuit board of optical waveguides according to the second embodiment of the present invention. However, the fourth embodiment is different from the first embodiment only in that the second circuit pattern 71 is formed inside the base substrate 10, instead of being formed inside the side substrate.

In other words, according to the third embodiment of the present invention, the second circuit pattern 71 may be formed inside the base substrate 10 and the upper surface of the second circuit pattern 71 may contact the lower surface of the side substrate 80.

Further, the printed circuit board for optical waveguides according to the third embodiment of the present invention may further include the third circuit pattern 72 that is formed inside the third insulating layer 40b configuring the upper substrate 40 and has the lower surface contacting the third adhesive layer 40a.

The printed circuit board for optical waveguides according to the third embodiment of the present invention as described above can obtain the same action and effect as the second embodiment of the present invention.

Next, the printed circuit board for optical waveguides according to the fourth embodiment of the present invention will be described in detail with reference to FIG. 5.

As shown in FIG. 5, a configuration of the printed circuit board for optical waveguides according to the fourth embodiment of the present invention is approximately similar to the configuration of the printed circuit board of optical waveguides according to the first embodiment of the present invention. However, the fourth embodiment is different from the first embodiment only in that it further includes an outer layer substrate 90 including a fourth adhesive layer 90a and a fourth insulating layer 90b that are sequentially stacked on the lower surface of the base substrate 10 and the upper surface of the upper substrate 40.

The fourth circuit pattern 91 may be formed on the upper surface of the outer substrate 90. A solder resist 100, which covers the fourth circuit pattern 91, may be formed on the outer layer substrate 90.

At this time, the fourth circuit patterns 91 formed on the upper and lower parts of the printed circuit board for optical waveguides according to the fourth embodiment of the present invention may be connected to each other by a via 105 that penetrates through the outer layer substrate 90, the upper substrate 40, the side substrate 80, and the base substrate 10.

The present embodiment shows and describes the outer layer substrate 90 including the fourth adhesive layer 90a and the fourth insulating layer 90b that are sequentially stacked, but the number of layers configuring the outer layer substrate 90 is not limited thereto.

The printed circuit board for optical waveguides according to the fourth embodiment of the present invention as described above can obtain the same action and effect as the first embodiment of the present invention and has an advantage capable of implementing a multilayer substrate.

<Embodiment of a Method of Manufacturing a Printed Circuit Board for Optical Waveguides>

Hereinafter, a method of manufacturing the printed circuit board for optical waveguides according to a first embodiment of the present invention will be described in detail with reference to FIGS. 6A to 6B.

FIGS. 6A to 6D are process cross-sectional views sequentially shown for explaining a method of manufacturing the printed circuit board for optical waveguides according to a first embodiment of the present invention.

Figure 6A:
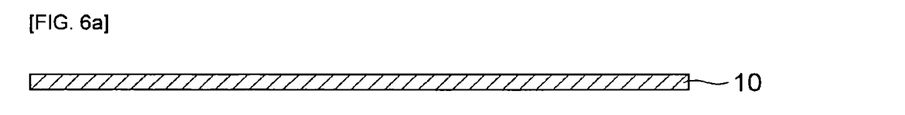
FIGS. 6A to 6D are process cross-sectional views sequentially shown for explaining a method of manufacturing the printed circuit board for optical waveguides according to the first embodiment of the present invention.

As shown in FIG. 6A, the base substrate 10 is prepared.

As the base substrate 10, the insulating layer, such as polyimide, etc., may be prepared. Further, as the base substrate 10, a metal foil, such as a copper foil, etc., may be prepared instead of the insulating layer or the laminate material of the insulating layer and the metal foil, etc., may be prepared.

Among others, when the insulation and the laminate of the metal foil are prepared as the base substrate 10, the second circuit pattern (see reference numeral '71' of FIG. 3) may be further formed by patterning the metal foil.

Figure 6B:
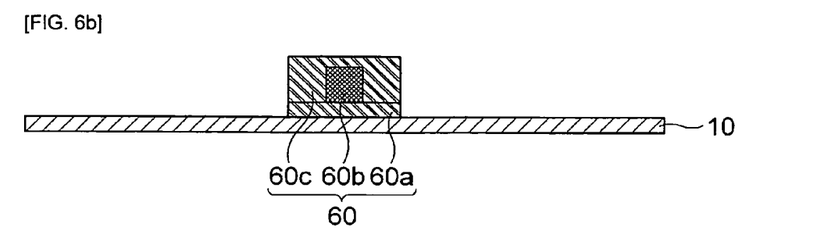

Then, as shown in FIG. 6B, the optical waveguide 60 is formed on the upper middle of the base substrate 10.

The optical waveguide 60 formed on the base substrate 10 includes the lower clad 60a, the core 60b that is formed on the upper middle of the lower clad 60a, and the upper clad 60c that is formed on the lower clad 60a to surround the upper surface and the side surface of the core 60b.

Although not shown herein, the optical waveguide 60 including the lower clad 60a, the core 60b, and the upper clad 60c may be formed as will be described below.

First, after the lower clad (not shown) is stacked on the base substrate 10, the lower clad layer, which is a part corresponding to an area in which the lower clad 60a will be formed, is selectively exposed. Herein, the lower clad layer may be formed in a film form, etc.

Thereafter, after the core layer (not shown) is formed on the lower clad layer, the core layer, which is a part corresponding to an area in which the core 60b will be formed, is selectively exposed.

At this time, instead of the method of exposing the core layer, an UV molding method of using a mold for forming the core 60b or a laser direct patterning method of removing one portion of the core layer using laser may be used.

Then, an unexposed part of the core layer and the lower clad layer is removed by a developer to form the lower clad 60a and the core 60b.

Next, the upper clad layer is formed on the base substrate 10 to cover the lower clad 60a and the core 60b. Next, after the upper clad layer, which is a part corresponding to the area in which the upper clad 60c will be formed, is selectively exposed, an unexposed part of the upper clad layer is removed by a developer to form the upper clad 60c.

Figure 6C:
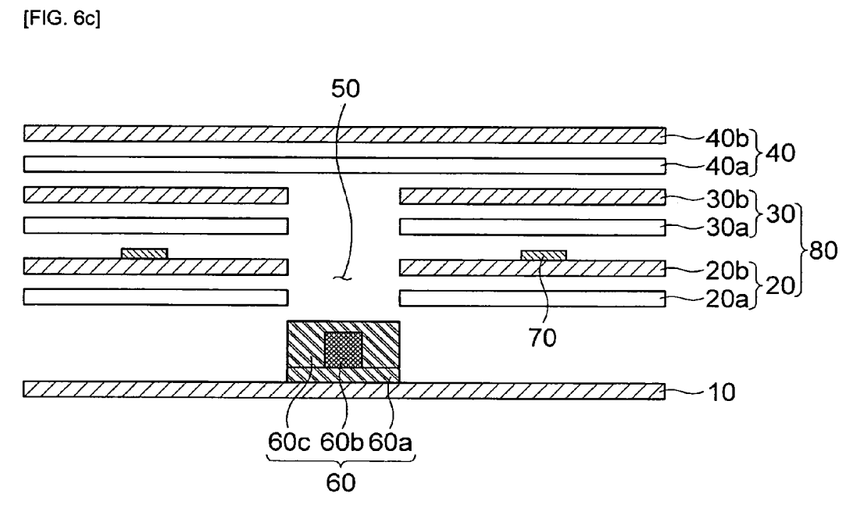

Next, as shown in FIG. 6C, the side substrate 80 including the through hole 50, through which the optical waveguide 60 penetrates, provided at the middle thereof is disposed on the upper part of the base substrate 10 on which the optical waveguide 60 is formed.

In the drawings, although the size of the through hole 50 is the same as the size of the optical waveguide 60, it is preferable that the size of the through hole 50 is formed to be larger than that of the optical waveguide 60.

This is to enable the optical waveguide 60 to easily penetrate inside the through hole 50 of the side substrate 80 in the stacking process of the substrates to be described below.

The side substrate 80 may include the first side substrate 20 having the first circuit pattern 70 formed on the upper surface thereof and the second side substrate 30 disposed on the first side substrate 20.

Herein, the first side substrate 20 may include the first adhesive layer 20a and the first adhesive layer 20b disposed on the first adhesive layer 20a and the second side substrate 30 may include the second adhesive layer 30a and the second insulating layer 30b disposed on the second adhesive layer 30a.

The first adhesive layer 20a, the first insulating layer 20b, the second adhesive layer 30a, and the second insulating layer 30b may be a film in a semi-curing state.

At this time, the first circuit pattern 70 may be formed on the upper surface of the insulating layer 20b configuring the first side substrate 20.

The first adhesive layer 20a and the first insulating layer 20b may be prepared separately as shown in the drawings and may be prepared in a mutually attached state similar to a coverlay.

The second insulating layer 30a and the second insulating layer 30b may be prepared separately or in a mutually attached state.

In the embodiment of the present invention, the first circuit pattern 70 preferably has thickness thinner than that of the optical waveguide 60 and more preferably, may have thickness much thinner than that of the core 60b.

Thereafter, the upper substrate 40 is disposed on the side substrate 80 on which the through hole 50 is formed. The upper substrate 40 may include the third adhesive layer 40a and the third insulating layer 40b that is disposed on the third adhesive layer 40a. At this time, the lower surface of the third insulating layer 40b may be formed with the third circuit pattern (see reference numeral '72' of FIG. 3).

Figure 6D:
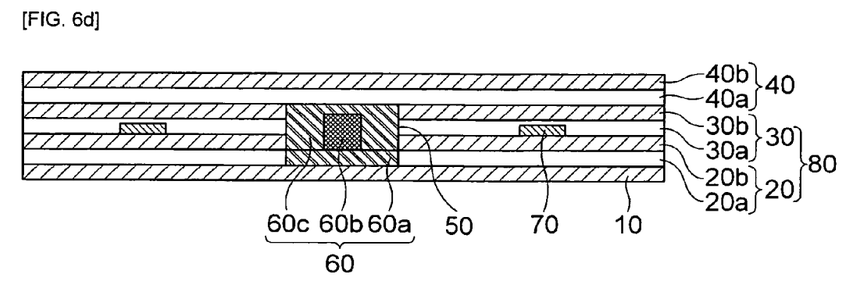

Thereafter, as shown in FIG. 6D, the side substrate 80 including the first circuit pattern 70 and the upper substrate 40 are stacked sequentially or in a lump on the base substrate 10 formed with the optical waveguide 60, so that the upper surface of the first circuit pattern 70 is positioned to be lower than the upper surface of the optical waveguide 60 and the lower surface thereof is positioned to be higher than the lower surface of the optical waveguide 60.

At this time, it is more preferable that the upper surface of the first circuit pattern 70 is positioned to be lower than the upper surface of the core 60b and the lower surface thereof is positioned to be higher than the lower surface of the core 60b.

Although not shown, the third adhesive layer 40a of the upper substrate 40 can flow in a space between the through hole 50 of the side substrate 80 and the optical waveguide 60 and can be filled in the space.

Next, another method of manufacturing the printed circuit board for optical waveguides according to a first embodiment of the present invention will be described in detail with reference to FIGS. 7A to 7B.

FIGS. 7A to 7F are process cross-sectional views sequentially shown for explaining another method of manufacturing the printed circuit board for optical waveguides according to a first embodiment of the present invention.

Figure 7A:
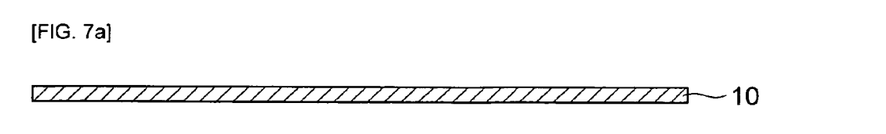
FIGS. 7A to 7F are process cross-sectional views sequentially shown for explaining another method of manufacturing the printed circuit board for optical waveguides according to the first embodiment of the present invention.

As shown in FIG. 7A, the base substrate 10 is prepared.

Figure 7B:
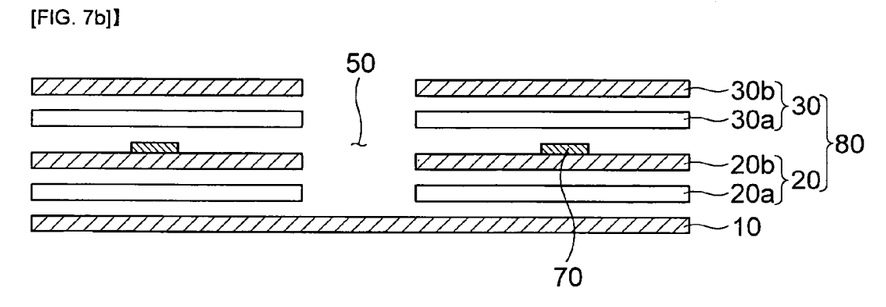

Thereafter, as shown in FIG. 7B, the side substrate 80, which includes the first side substrate 20 having the through hole 50 provided at the middle thereof and the first circuit pattern 70 formed on the upper surface thereof and the second side substrate 30, is disposed on the base substrate 10.

The first side substrate 20 may include the first adhesive layer 20a and the first adhesive layer 20b disposed on the first adhesive layer 20a and the second side substrate 30 may include the second adhesive layer 30a and the second insulating layer 30b disposed on the second adhesive layer 30a.

The first adhesive layer 20a, the first insulating layer 20b, the second adhesive layer 30a, and the second insulating layer 30b may be a film in a semi-curing state.

At this time, the first circuit pattern 70 may be formed on the upper surface of the insulating layer 20b configuring the first side substrate 20.

Figure 7C:
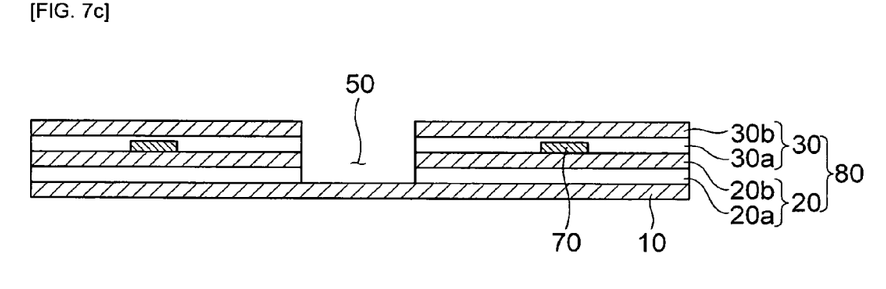

Next, as shown in FIG. 7C, the first side substrate 20 and the second side substrate 30 are stacked sequentially or in a lump on the base substrate 10.

Figure 7D:
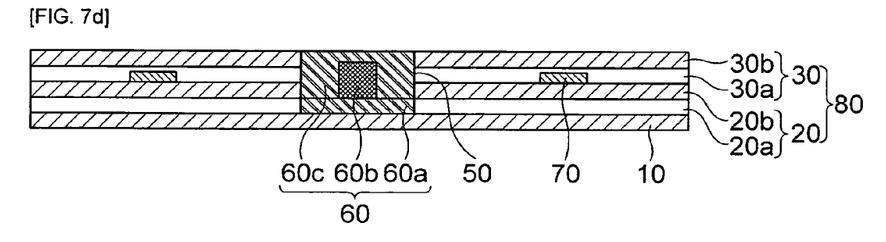

Then, as shown in FIG. 7D, the optical waveguide 60 is formed inside the through hole 50 of the side substrate 80.

The optical waveguide 60 formed on the base substrate 10 includes the lower clad 60a, the core 60b that is formed on the upper middle of the lower clad 60a, and the upper clad 60c that is formed on the lower clad 60a to surround the upper surface and the side surface of the core 60b.

Herein, the optical waveguide 60 preferably has thickness thicker than that of the first circuit pattern 70 and more preferably, the core 60b configuring the optical waveguide 60 may have thickness thicker than that of the first circuit pattern 70.

In addition, in forming the optical waveguide 60, it is preferable that the upper surface of the first circuit pattern 70 formed on the side substrate 80 may be positioned to be lower than the upper surface of the optical waveguide 60 and the lower surface thereof may be positioned to be higher than the lower surface of the optical waveguide 60. More preferably, the upper surface of the first circuit pattern 70 may be positioned to be lower than the upper surface of the core 60b and the lower surface thereof may be positioned to be higher than the lower surface of the core 60b.

Figure 7E:
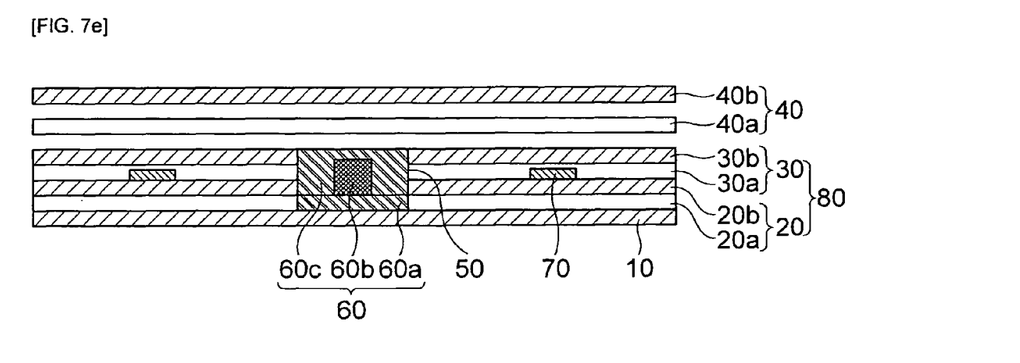

Then, as shown in FIG. 7E, the upper substrate 40 is disposed on the side substrate 80 including the optical waveguide 60.

The upper substrate 40 may include the third adhesive layer 40a and the third insulating layer 40b that is disposed on and the third adhesive layer 40a. The third adhesive layer 40a and the third insulating layer 40b may be a film in a semi-curing state.

Figure 7F:
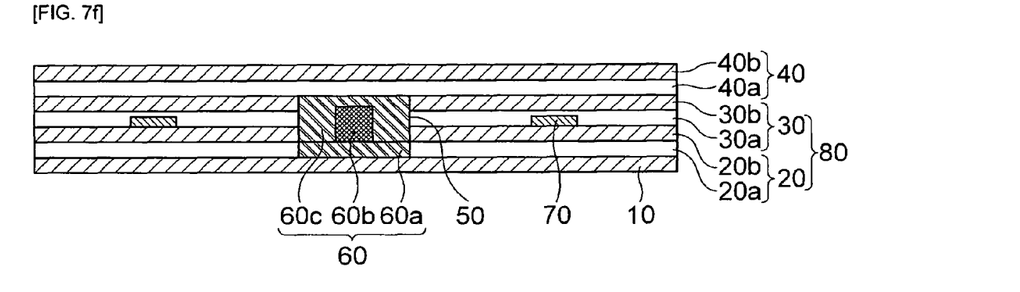

Then, as shown in FIG. 7F, the upper substrate 40 is stacked on the side substrate 80 including the optical waveguide 60.

As shown in the drawings, the filling amount of the upper clad 60c is sufficiently provided at the time of forming the optical waveguide 60, so that the optical waveguide 60 is formed at the same size as the through hole 50, thereby making it possible to omit the stacking process of the upper substrate 40 when there is no a spaced space between the optical waveguide 60 and the through hole 50.

Meanwhile, the optical waveguide 60 is formed at a smaller size than the through hole 50 at the time of forming the optical waveguide 50, such that the spaced space between the optical waveguide 60 and the through hole 50 can occurr.

In this case, as described above, the third adhesive layer 40a in a semi-curing state that configures the upper substrate 40 by performing the stacking process of the upper substrate 40 can flow in the space between the optical waveguide 60 and the through hole 50 and can be filled in the space.

Next, another method of manufacturing the printed circuit board for optical waveguides according to the first embodiment of the present invention will be described in detail with reference to FIGS. 7A to 7I.

FIGS. 8A to 8I are process cross-sectional views sequentially shown for explaining another method of manufacturing the printed circuit board for optical waveguides according to the first embodiment of the present invention.

As shown in FIG. 8A, the base substrate 10 is prepared.

Thereafter, as shown in FIG. 8B, the first side substrate including the through hole 50 provided at the middle thereof is disposed on the base substrate 10. The first side substrate may be made of the first adhesive layer 20a. Next, a metal foil 70a is disposed on the first adhesive layer 20a that is the first side substrate.

Thereafter, as shown in FIG. 8C, the first adhesive layer 20a and the metal foil 70a are stacked on the base substrate 10.

Next, as shown in FIG. 8D, the first circuit pattern 70 is formed on the first adhesive layer 20a by removing a part of the metal foil 70a.

Thereafter, as shown in FIG. 8E, the second side substrate 30 including the through hole 50 provided at the middle thereof is disposed on the first adhesive layer 20a on which the first circuit pattern 70 is formed, similar to the first adhesive layer 20a.

The second side substrate 30 may include the second adhesive 30a and the second insulating layer 30b in a semi-curing state.

Thereafter, as shown in FIG. 8F, the second side substrate 30 is stacked on the first adhesive layer 20a on which the first circuit pattern 70 is formed.

Thereafter, as shown in FIG. 8G, the optical waveguide 60 is formed inside the through hole 50 of the side substrate 80 that includes the first side substrate and the second substrate 30.

The optical waveguide 60 includes the lower clad 60a, the core 60b that is formed on the upper middle of the lower clad 60a, and the upper clad 60c that is formed on the lower clad 60a to surround the upper surface and the side surface of the core 60b.

Herein, the optical waveguide 60 preferably has thickness thicker than that of the first circuit pattern 70 and more preferably, the core 60b configuring the optical waveguide 60 may have thickness thicker than that of the first circuit pattern 70.

In addition, in forming the optical waveguide 60, it is preferable that the upper surface of the first circuit pattern 70 formed on the side substrate 80 is positioned to be lower than the upper surface of the optical waveguide 60 and the lower surface thereof is positioned to be higher than the lower surface of the optical waveguide 60. More preferably, the upper surface of the first circuit pattern 70 may be positioned to be lower than the upper surface of the core 60b and the lower surface thereof may be positioned to be higher than the lower surface of the core 60b.

Next, as shown in FIG. 8H, the upper substrate 40 including the third adhesive layer 40a and the third insulating layer 40b is disposed on the side substrate 80 including the optical waveguide 60.

Then, as shown in FIG. 8I, the upper substrate 40 is stacked on the side substrate 80 including the optical waveguide 60.

Next, a method of manufacturing the printed circuit board for optical waveguides according to a third embodiment of the present invention will be described in detail with reference to FIGS. 9A to 9E.

FIGS. 9A to 9E are process cross-sectional views sequentially shown for explaining a method of manufacturing the printed circuit board for optical waveguides according to a third embodiment of the present invention.

Figure 9A:
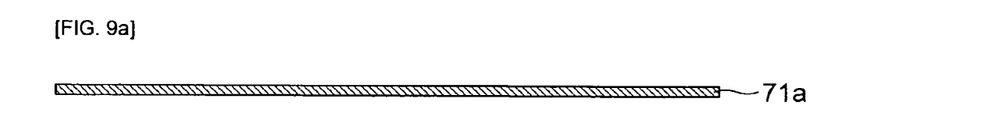
FIGS. 9A to 9E are process cross-sectional views sequentially shown for explaining a method of manufacturing the printed circuit board for optical waveguides according to the third embodiment of the present invention.

As shown in FIG. 9A, a first metal foil 71a is prepared.

Figure 9B:
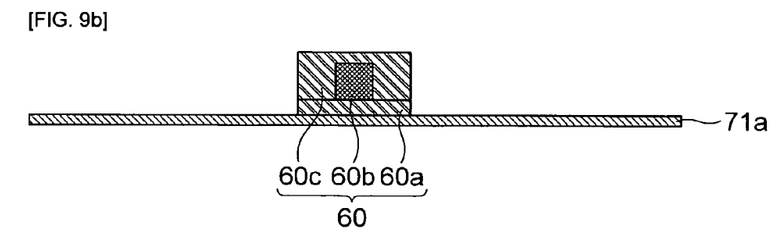

Then, as shown in FIG. 9B, the optical waveguide 60, which includes the lower clad 60a, the core 60b, and the upper clad 60c, is formed on the upper middle of the first metal foil 71a.

Figure 9C:
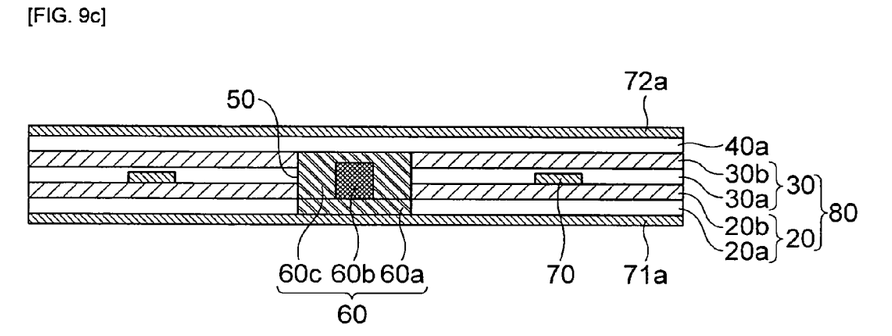

Next, as shown in FIG. 9C, the side substrate 80 including the through hole 50, through which the optical waveguide 60 penetrates, provided at the middle thereof is stacked on the metal foil 71a on which the optical waveguide 60 is formed.

The side substrate 80 may include the first side substrate 20 having the first circuit pattern 70 formed on the upper surface thereof and the second side substrate 30 stacked on the first side substrate 20.

The first side substrate 20 may include the first adhesive layer 20a and the first insulating layer 20b that are sequentially stacked and the second side substrate 30 may include the second adhesive layer 30a and the second insulating layer 30b that are sequentially stacked.

Herein, the first circuit pattern 70 preferably has thickness thinner than that of the optical waveguide 60 and more preferably, may have thickness much thinner than that of the core 60b.

It is preferable that the upper surface of the first circuit pattern 70 is positioned to be lower than the upper surface of the optical waveguide 60 and the lower surface thereof is positioned to be higher than the lower surface of the optical waveguide 60, when the side substrate 80 is stacked.

More preferably, the upper surface of the first circuit pattern 70 may be positioned to be lower than the upper surface of the core 60b and the lower surface thereof may be positioned to be higher than the lower surface of the core 60b.

Thereafter, the third adhesive layer 40a and a second metal foil 72a are sequentially stacked on the side substrate 80 including the optical waveguide.

Figure 9D:
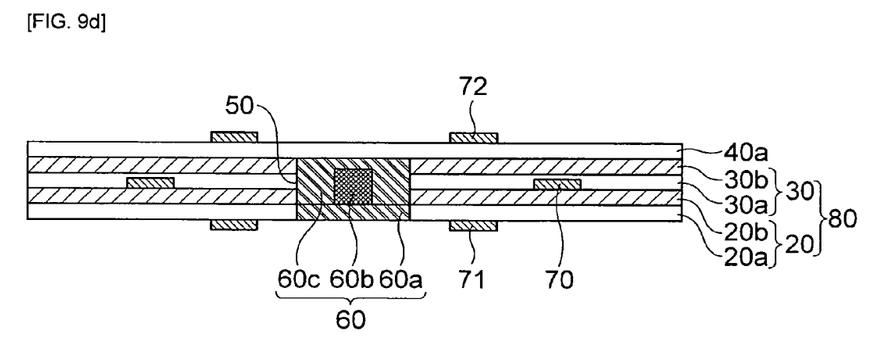

Then, as shown in FIG. 9D, the second circuit pattern 71 is formed on the lower surface of the first adhesive layer 20a of the first side substrate 20 and the third circuit pattern 72 is formed on the upper surface of the third adhesive layer 40a by removing a part of the first metal foil 71a and the second metal foil 72a.

Figure 9E:
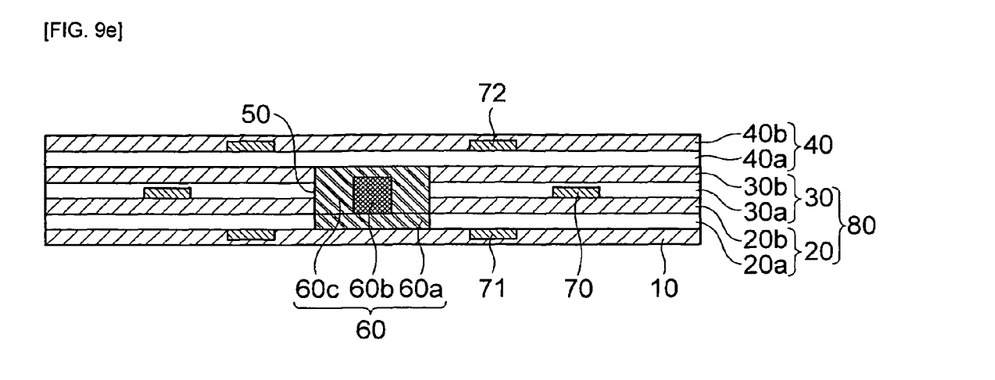

Thereafter, as shown in FIG. 9E, the base substrate 10, which covers the second circuit pattern 71, is formed on the lower surface of the first side substrate 20 and the third insulating layer 40b, which covers the third circuit pattern 72, is formed on the upper surface of the third adhesive layer 40a.

The base substrate 10 may be made of an insulating layer such as polyimide, etc.

While this invention has been described in connection with what is presently considered to be practical exemplary embodiments, many substitutions, changes and modifications can be made by those skilled in the art to which the present invention pertains without departing from the spirit of the invention, but it should be considered that all such modifications are included within the spirit and scope of the appended claims.

What is claimed is:

1. A printed circuit board, comprising:
  a base substrate;
  an optical waveguide that is formed on an upper middle of the base substrate and includes a lower clad, a core formed on an upper middle of the lower clad, and an upper clad formed on the lower clad to surround an upper surface and a side surface of the core; and
  a side substrate that is formed on the base substrate and has a through hole, through which the optical waveguide penetrates, provided at a middle of the side substrate and a circuit pattern formed in the side substrate,
  an upper surface of the circuit pattern being lower than an upper surface of the optical waveguide and a lower surface of the circuit pattern being higher than a lower surface of the optical waveauide.

2. The printed circuit board according to claim 1, wherein a thickness of the circuit pattern is smaller than a thickness of the optical waveguide.

3. The printed circuit board according to claim 1, wherein a thickness of the circuit pattern is smaller than a thickness of the core.

4. The printed circuit board according to claim 1, wherein,
  the upper surface of the circuit pattern is lower than the upper surface of the core and the lower surface of the circuit pattern is higher than a lower surface of the core.

5. The printed circuit board according to claim 1, further comprising an upper substrate that is formed on the side substrate.

6. The printed circuit board according to claim 5, wherein the upper substrate includes an adhesive layer and an insulating layer that are sequentially stacked.

7. A printed circuit board, comprising:
  a base substrate;
  an optical waveguide that is formed on an upper middle of the base substrate and includes a lower clad, a core formed on an upper middle of the lower clad, and an upper clad formed on the lower clad to surround an upper surface and a side surface of the core; and
  a side substrate that is formed on the base substrate and has a through hole, through which the optical waveguide penetrates, provided at a middle of the side substrate and a circuit pattern formed in the side substrate,
  an upper surface of the circuit pattern being lower than the upper surface of the core and a lower surface of the circuit pattern being higher than a lower surface of the core.

* * * * *

UNITED STATES PATENT AND TRADEMARK OFFICE
CERTIFICATE OF CORRECTION

PATENT NO. : 8,036,501 B2  
APPLICATION NO. : 12/588453  
DATED : October 11, 2011  
INVENTOR(S) : Sang Hoon Kim et al.

Page 1 of 1

It is certified that error appears in the above-identified patent and that said Letters Patent is hereby corrected as shown below:

IN THE CLAIMS:

Column 14, Line 15 (Approx.), in claim 1, delete "waveauide." and insert -- waveguide. --, therefor.

Signed and Sealed this
Thirty-first Day of January, 2012

David J. Kappos
*Director of the United States Patent and Trademark Office*